US010774275B2

(12) United States Patent
Kirchmann et al.

(10) Patent No.: US 10,774,275 B2
(45) Date of Patent: Sep. 15, 2020

(54) APPARATUS AND METHOD FOR INVESTIGATING NAPHTHA REFORMING PROCESSES

(71) Applicant: hte GmbH the high throughput experimentation company, Heidelberg (DE)

(72) Inventors: Marius Kirchmann, Eppelheim (DE); Christoph Hauber, Lorsch (DE)

(73) Assignee: hte GmbH the high throughput experimentation company, Heidelberg (DE)

( * ) Notice: Subject to any disclaimer, the term of this patent is extended or adjusted under 35 U.S.C. 154(b) by 324 days.

(21) Appl. No.: 15/541,403

(22) PCT Filed: Dec. 22, 2015

(86) PCT No.: PCT/EP2015/080911
§ 371 (c)(1),
(2) Date: Jul. 3, 2017

(87) PCT Pub. No.: WO2016/110408
PCT Pub. Date: Jul. 14, 2016

(65) Prior Publication Data
US 2018/0010058 A1 Jan. 11, 2018

(30) Foreign Application Priority Data
Jan. 5, 2015 (DE) .................. 10 2015 200 035

(51) Int. Cl.
*C10G 59/06* (2006.01)
*C10G 35/24* (2006.01)
(Continued)

(52) U.S. Cl.
CPC .......... *C10G 59/06* (2013.01); *B01J 19/0006* (2013.01); *B01J 19/0013* (2013.01);
(Continued)

(58) Field of Classification Search
None
See application file for complete search history.

(56) References Cited

U.S. PATENT DOCUMENTS 4,251,870 A * 2/1981 Jaffe .................. G01N 33/2829
700/268
7,118,917 B2 10/2006 Bergh et al.
(Continued)

FOREIGN PATENT DOCUMENTS

| DE | 2 224 637 A1 | 11/1972 |
| WO | WO 02/14854 A1 | 2/2002 |
| WO | WO 2005/063372 A2 | 7/2005 |

OTHER PUBLICATIONS

International Preliminary Report on Patentability and Written Opinion dated Jul. 20, 2017 in PCT/EP2015/080911 (with English language translation).
(Continued)

*Primary Examiner* — Renee Robinson
*Assistant Examiner* — Derek N Mueller
(74) *Attorney, Agent, or Firm* — Oblon, McClelland, Maier & Neustadt, L.L.P.

(57) ABSTRACT

An apparatus and a method are used for investigating the naphtha reforming process in catalyst test devices with reactors arranged in parallel. The apparatus has a plurality of reactors arranged in parallel with reaction chambers (R1, R2, . . . ), a product fluid supply, a process control, and at least one analysis unit. Each individual reactor has an outlet line for the product fluid stream, wherein the analysis unit is operatively connected to each outlet line for the product fluid stream and the apparatus is functionally connected to the control of the apparatus. In carrying out the method, naphtha-containing reactant fluid streams are brought into contact with catalysts in the individual reactors and the product fluid streams are subsequently supplied to the online (Continued)

analysis unit from the respective outlet lines of the individual reactors and analyzed. Using the evaluation of the online analytical characterization data, the process parameters of the respective reactor unit are adapted. The process steps of analytical characterization, evaluation, and adaptation of process parameters are repeated for the duration of the investigation.

15 Claims, 6 Drawing Sheets

(51) Int. Cl.
      *B01J 19/00*      (2006.01)
      *B01J 19/24*      (2006.01)
      *G01N 31/10*      (2006.01)
      *G01N 33/28*      (2006.01)

(52) U.S. Cl.
    CPC ....... *B01J 19/0046* (2013.01); *B01J 19/2425* (2013.01); *C10G 35/24* (2013.01); *G01N 31/10* (2013.01); *G01N 33/28* (2013.01); *B01J 2219/00051* (2013.01); *B01J 2219/00164* (2013.01); *B01J 2219/00286* (2013.01); *B01J 2219/00389* (2013.01); *B01J 2219/00418* (2013.01); *B01J 2219/00495* (2013.01); *B01J 2219/00702* (2013.01); *B01J 2219/00747* (2013.01)

(56) References Cited

U.S. PATENT DOCUMENTS

2002/0182735 A1    12/2002    Kibby et al.
2013/0323853 A1    12/2013    Disanzo et al.

OTHER PUBLICATIONS

International Search Report and Written Opinion dated Mar. 29, 2016 in PCT/EP2015/080911 (with English language translation).

Henri L'Oncle, "Automatisation d'une unite pilote de reforming catalytique," L'Industrie du Petrole en Europe Gaz-Chimie, vol. 36, Issue 388, May 1968, pp. 54-55.

Vincent Knop, et al., "A Linear-by-Mole Blending Rule for Octane Numbers of N-Heptane/Iso-Octane/Toluene Mixtures", Fuel, vol. 115, 2014, pp. 666-673.

Dr. J. Patrick Kennedy, "New Control Package Is Aid to Cat Reforming", Oil and Gas Journal, vol. 77, Issue 39, 1979, pp. 191-200.

\* cited by examiner

APPARATUS AND METHOD FOR INVESTIGATING NAPHTHA REFORMING PROCESSES

The present invention relates to a method, preferably a laboratory method, for investigating naphtha reforming processes in catalyst test devices, preferably in catalyst test devices with reactors arranged in parallel.

Naphtha reforming is used for catalytically reacting gasoline base stock (naphtha) and light oils in order to convert these into higher-grade fuels (gasoline) and chemicals (aromatics). Because of the high demand for fuels and basic chemicals, naphtha reforming is of great economic and technical importance. Moreover, naphtha reforming yields hydrogen, which is urgently needed for hydroprocessing in refineries. The further development and improvement of naphtha reforming is of particular interest in order to increase the yield of reformates (gasoline, aromatics) per barrel of naphtha and thus conserve precious resources.

The present document relates to this utilization of catalyst test devices for carrying out naphtha reforming in the laboratory field or in the area of pilot facilities in order to improve the process parameters for naphtha reforming and/or develop new catalysts. The investigation results obtained in pilot facilities make it possible to improve industrial-scale processes and are of great value for the industrial sectors of catalyst manufacturing and the petrochemical industry, in which naphtha processing is carried out.

Even minor improvements in industrial-scale naphtha reforming have a major effect on its economic efficiency and thus the associated energy costs, as the industrial dimensions thereof are significant. However, there are limitations on laboratory methods using catalyst test devices, as the implementation of industrial-scale processes using laboratory equipment is subject to numerous sources of error and fluctuations. As a consequence, these minor improvements can be detected either not at all or only to an insufficient degree because of fluctuations in measurement accuracy.

A particular parameter that must be monitored and/or optimized in naphtha reforming is the so-called "octane number." The octane number is an indicator of the anti-knock characteristics of gasolines and is thus a metric for the quality of gasolines. The anti-knock characteristics of gasolines are determined using engine test stands, and a distinction is made between the "RON" (i.e. research octane number) and the MON (motor octane number). The MON relates to the anti-knock characteristics of a gasoline determined at an engine speed of 900 rpm. The RON relates to the anti-knock characteristics of a gasoline determined at an engine speed of 600 rpm. For determination of the RON and MON using an engine test stand, one half liter of a gasoline mixture is required in each case. In the US, these numbers pertain to the average values determined for RON and MON (i.e. the octane number is derived from (RON+MON)/2).

Determination of the octane number with laboratory equipment by using analytical characterization methods during reforming other than determination of anti-knock characteristics of gasolines on engine test stands is of great importance, first in order to avoid production of samples in half liter scale, which is extremely costly. Second, this would yield excessively low time resolution of the octane number, as these samples would have to be collected over a long period and would therefore yield only an average value over the time interval.

It is known in principle from the prior art that the octane number can be calculated by means of analytical measurements, in particular by gas chromatography and near infrared spectroscopy. For determining the octane number by means of gas chromatography, the composition of the reformate is first determined, and the octane number is then determined using octane number models. For an overview, reference is made herein to the publication by Knop et al. in Fuel 115 (2014) 666-673, in which various octane number models are presented and evaluated.

Methods for investigating naphtha reforming in the laboratory are known in principle from the prior art. In naphtha reforming, naphtha is usually brought into contact with platinum-containing bifunctional catalysts, which contain finely-dispersed platinum on (usually chlorinated) aluminum oxide. In addition, bi- or multimetallic catalysts are increasingly being used.

In principle, catalyst test stands for investigation of catalysts in the laboratory are generally known in the prior art. For example, U.S. Pat. No. 7,118,917 B2 by Bergh et al. discloses a method and an apparatus with four or more reactors arranged in parallel in which individual heating of the individual reactors is possible. Moreover, the reactors can be heated along the reactor axis in different heating zones to different temperatures in order to thus ensure more precise temperature control in the reactors. Reaction apparatuses with reactors arranged in parallel, which are suitable in principle for the testing of catalysts, are also known. An example of this is presented in US 2002/0182735 A1 by Chuck Kibby et al., which was filed by Chevron Texaco Corporation with the US Patent Office on May 28, 2002. In reactors arranged in parallel, the products can be examined with respect to their properties, wherein optimized catalysts for a predetermined product flow are to be obtained using combinatorial methods.

One of the objects of the present invention is to specifically adapt the method for investigating catalysts in parallel facilities with respect to naphtha reforming processes and to improve said method with respect to the methods of prior art. A fundamental technical problem to be solved is the insufficient accuracy of laboratory methods, which are fraught with statistical errors, with the result that reliability is sharply limited or no significant reliability is possible on a laboratory scale.

The objects mentioned here and numerous further objects not mentioned here are achieved by means of an apparatus and a method, which are described in further detail below:

Apparatus

The apparatus according to the invention has a plurality of reactors arranged in parallel, preferably tubular reactors, wherein the apparatus is suitable for investigating naphtha reforming, wherein the apparatus furthermore has a process control and a product fluid supply (common to all or a plurality of the reactors), and each individual reactor has its own outlet line for product flow as well as at least one online analysis unit, wherein each individual reactor of the plurality of reactors further is equipped with a separate heating system, and wherein the apparatus is characterized in that the analysis unit is operatively connected with each outlet line for the product fluid stream.

The analysis unit preferably works "online", i.e. there is at least temporarily a fluid connection between a reactor outlet and the sample inlet of the analysis unit. This further means that the product fluid stream, or an aliquot thereof, is directly transferred to an analysis unit. Preferably, no manual manipulation of the sample is required at this point. The analysis unit can directly and immediately evaluate the analysis results and transfer them to the control unit. In such an "online" analysis unit, the time between physical measurement of the parameters in the product fluid stream and transfer of the measurement data to the control unit is preferably less than 100 milliseconds, more preferably less than 10 milliseconds, and most preferably less than 1 millisecond. The times required for transferring the measurement data to the control unit are very short overall.

In a further embodiment, two or more reactors are located in the respective outlet line, and a multiport or selection valve is located on the inlet side of the analysis unit. This valve is configured such that an operative connection is always simultaneously established precisely between a reactor effluent and the analysis unit (this corresponds to multiplexing).

Selection of the operative connection and thus the reactor effluent is controlled and initiated by the process control. The results of the analysis unit are stored in the process control such that they can be assigned with respect to both time and value to the reactor from which the product fluid was withdrawn. The change in the variable parameters of a reactor takes place based on these assigned data (=demultiplexing).

By means of this online analysis unit, the fluid streams from the individual outlet lines can be analyzed sequentially and/or in parallel.

The present invention relates in a preferred embodiment to an apparatus for investigating naphtha reforming, wherein the apparatus comprises:
a plurality of reactors arranged in parallel with reaction chambers (R1, R2, . . . ),
a product fluid supply common to two or more of these reactors,
a process control, and
an analysis unit,
wherein each individual reactor has an outlet line for the product fluid stream,
characterized in that the analysis unit is operatively connected to each outlet line for the product flow, and in that the analysis unit is functionally connected to the control of the apparatus,
wherein the analysis unit is suitable for analysis of a gaseous or vaporous product fluid stream respectively, and the analysis unit, together with the process control, allows the determination and optimization of an octane number in the reactors arranged in parallel.

Method

The object of the invention was further solved in that by means of an analysis unit, preferably an analysis unit comprising gas chromatography, the product composition is individually analyzed for each reactor in the parallel facility, wherein in particular and preferably, the product fluid for this analysis does not have to be condensed, or at least not to a significant degree. In this case, it is of particular importance in the method according to the invention that transport of the part of the product to be analyzed takes place in the gas phase and is not accompanied by any condensation.

The invention relates to a method carried out using the apparatus according to the invention, in which method a naphtha-containing reactant fluid stream is supplied to each individual reactor of the plurality of reactors R1, R2, is brought into contact in the respective reactor with a catalyst at a temperature in the range of 100° C. to 600° C., and preferably in the range of 400 to 550° C., and is converted to one product fluid stream each. Each individual product fluid stream is fed via the individual outlet lines to a product fluid receptacle or an afterburner. In this method, each of the individual product fluid streams or partial streams of the individual outlet lines is subjected to the following process steps:
(i) analytical characterization by means of an analysis unit, including the individual product fluid streams, wherein the analysis relates to quantification of one or a plurality of components, preferably one or a plurality of groups of 10 to 20 components each, and more preferably 10 groups of 1 to 100 components each,
(ii) calculation of the octane number and comparison of the calculated octane number with a set value,
(iii) calculation of the temperature difference required to keep the octane number constant,
(iv) adaptation of the temperature of the respective heating system surrounding the reactor, from the outlet line of which a product flow was analyzed,
at least one repetition of the process steps (i) through (iv) by analyzing the product fluid stream that is discharged from the respective outlet lines, and calculation of the respective octane number that characterizes the product fluid stream.

According to a preferred embodiment, the present invention relates to a method for investigating naphtha reforming using an apparatus as described herein, wherein the naphtha-containing reactant fluid stream containing the components of at least one hydrocarbon from the group with 5 to 14 carbon atoms, preferably a mixture of hydrocarbons with 5 to 14 carbons, and hydrogen with a hydrogen content in the range of 0.5-60 vol. %, and preferably 10-30 vol. %, is supplied to the individual reactors R1, R2, is brought into contact in the respective reactors with a catalyst at a temperature in the range of 100° C. to 600° C., and preferably in the range of 400° C. to 550° C., and is converted to one product fluid stream each,
and this product fluid stream is subsequently supplied to an outlet line, wherein the method is characterized by the following process steps:
(i) analytical characterization of the individual product fluid streams by means of an analysis unit, wherein the analysis relates to quantification of one or a plurality of components, preferably one or a plurality of groups of 1 to 300 components each, and more preferably four groups of 20 to 150 components each,
(ii) comparison of the result value of quantitation with a set value, wherein the comparison comprises storage of an evaluation model,
(iii) adaptation of a process parameter that relates to the reaction process of the respective reactor from the outlet line of which the product fluid stream was analyzed, and repetition of the process steps (i) through (iii) by analyzing the product fluid stream that is discharged from the respective outlet lines.

With respect to the term common product fluid supply, reference is made to the publication of PCT Application WO 2005/063372 A2 (with the priority date of 23 Dec. 2003) by the same applicant. In PCT Application WO 2005/063372 A2, the meaning of the terms repressurization gas and pressurization gas is also disclosed. Moreover, although the present invention is preferred for parallel reactor apparatuses, it is not limited to parallel reactor apparatuses, but also comprises individual reactors that are constructed according to the present disclosure (but without comprising two or more reactors). In particular, using GC and without condensation, the method according to the invention also provides the advantages according to the invention for an individual reactor.

Within the meaning of the present invention, the product fluid stream preferably contains less than 1% condensed product fluid, and more preferably less than 0.5%.

Calculation of the octane number required for step (ii) is carried out using suitable octane number models from the product composition. Here, among other functions, a software-supported algorithm is used to evaluate the chromatograms, determine the product composition, and calculate the octane number. The temperature adaptation is then carried out by means of the corresponding octane number-temperature ratio of the respective catalyst determined in advance. This is then transmitted to the respective reactor heater as a temperature difference in order to keep the octane number constant.

The method according to the invention comprises the process steps (i) through (iii), which constitute a control loop. Conducting of the process steps and implementation of the control loop account for the entire duration of the method according to the invention. Implementation of the control loop is preferably carried out with respect to each individual reactor for at least 2 to 10 cycles of the control loop. The number of cycles of the control loop depends among other factors on the total duration of the catalytic investigation. If the catalysts are tested for a period of weeks or months, the number of cycles of the control loop can be correspondingly high. With respect to the number of cycles, the deactivation rate of the individual catalysts is also to be taken into account. In the case of rapidly deactivating catalysts, it is preferable to run through the control group more frequently than in the case of slowly deactivating catalysts.

An evaluation of chromatograms obtained by gas chromatography is preferred.

Evaluation of the chromatograms preferably comprises the identification of individual components or groups of components. In particular, high accuracy can be achieved by the use of GC as an analysis method, especially in "online" operation, which is particularly beneficial for the method according to the invention. Preferably, comparative data are used in evaluation of the measurement data that were preferably generated in the process of calibration.

Because of the high complexity of the multicomponent mixtures, online analytical characterization can require a duration in the area of several minutes. This duration of the analysis and the use of the preferred evaluation model are advantageous in that the accuracy of the method according to the invention is sharply increased compared to the methods of prior art, primarily with respect to time resolution. The time resolution for the investigation of deactivation processes is also derived from the duration of analysis of online analytical characterization.

The analytical characterization of the product fluid stream, preferably in the online mode, is thus the time-determining step. The online analytical characterization is in a range of 0.1-300 min, preferably in a range of 1-150 min, more preferably in a range of 10-40 min. In an alternative embodiment of the method according to the invention, characterization of the product fluid stream is carried out by means of IR spectroscopy. Just as in GC characterization, corresponding calibration data and methods are stored in the control unit, by means of which analysis of the components and determination of the octane number are carried out.

This duration of the actual analysis is to be distinguished from the duration of transfer of the data from analysis unit to control unit, which was described above and lies in the millisecond range. Therefore, the duration of the data transfer is also not the step that decisively influences the rate of the method according to the invention.

It is also to be noted here that many of the catalysts used for reforming naphtha-containing reactant streams generally have sufficiently long service lives and do not show rapid deactivation. The duration of carrying out the online analytical characterization and the intervals for repetition of the control loop are therefore sufficient in relation to the deactivation rate of the individual catalysts.

Moreover, in a further embodiment, however, the test apparatus and the method can also be configured such that the duration of repetition of the individual cycles of the control loop can be correspondingly adapted. In particularly preferred embodiments of the method, for example, this adaptation can consist of preferably using a multichannel GC. By means of the multichannel GC, the product fluid streams of a plurality of reactors can be analyzed at the same time. Moreover, is it also preferable to equip the apparatus with more than one online analysis unit. Particularly preferred embodiments are an apparatus with at least one group of four reactors arranged in parallel and one dual-channel GC. Particularly preferred is an apparatus with eight reactors arranged in parallel and one to two multichannel GC's. The multichannel GC's should preferably be dual-channel GC's, which simultaneously characterize the product fluid streams of two reactors.

A further preferred aspect of the method according to the invention is the statistical evaluation of the data, wherein this statistical evaluation is based on an evaluation model that was stored in the process control before carrying out the catalytic test investigations. The evaluation model and comparison between the actual and set values also relate to the plausibility check of the data and the evaluation of the process parameters to be newly used. In particular, preferred process parameters are pressure in the reactor, reactor temperature, fluid stream flow rate, and the composition of the fluid stream. Co-feeds can also be added to the reactant fluid. The method can thus be carried out at least with respect to the control of four process parameters. It is preferable for the method according to the invention to be carried out such that the method-determining process parameter is formed in each case by the reactor temperature of the individual reactors. In this case, it is important within the framework of the device according to the invention for the reactors to be capable of being individually heated. Such individual heating is not routinely provided for test stands, and in most cases, it is neither necessary nor beneficial—but the opposite is the case in the present reforming method.

With respect to the product fluid supply, the method according to the invention is characterized by a WHSV of 0.1 to 50 $h^{-1}$ and preferably a WHSV of 0.5 to 5 $h^{-1}$.

With respect to the control loop, this should preferably be an embodiment with a fuzzy logic controller. This algorithm addresses the problem of how to handle outliers within the analysis report. This includes the detection and discarding of peaks. The actual control algorithm ultimately constitutes an approximation algorithm. Examples of an approximation algorithm include simplex approximation, interval nesting, and similar algorithms.

A plurality of process parameters can be adjusted in the method according to the invention. For example, the three parameters temperature, pressure, and input flows can be varied. As described above, the composition of the reactant fluid can also be varied. This variability is also a special feature of the method according to the invention.

The method according to the invention relates to catalytic naphtha reforming on the laboratory scale and provides the foundation for a simulation in order to make precise predictions on a small scale of the behavior of catalysts and process conditions in industrial-scale processes. In principle, the naphtha precursors or reactants are subjected to refining by means of the catalytic process. The method according to the invention is therefore configured to be controlled in such a way that predetermined target characteristics are achieved in the product flow stream via the presence of certain desirable chemical components. The product characteristics play a decisive role in evaluation and are crucial for adapting the control parameters, wherein precise analytical evaluation is carried out.

The method relates to the continuous determination of the characteristic values of the target components and suitable adaptation of the process parameters in order to ensure that the target properties will be achieved.

A particularly preferred target property of the product fluid stream is the obtaining of a predetermined octane number in the reformate. The method is preferably configured such that the online analytical characterization is carried out using a model that provides highly accurate evaluation.

The method according to the invention is characterized by high accuracy. Compared to the prior art, the accuracy that can be achieved by means of the invention is comparable to that of pilot facilities that operate as single-strand (i.e. not parallel) facilities and in connection with condensation of product fluids.

A method for operating an industrial-scale facility is described for example in DE 2224637. In the method of DE 2224637, the reaction effluent is analyzed. This analysis is carried out in order to determine a performance parameter and a total conversion parameter. The performance value is determined by means of an optimizer device, and the intensity of the reaction is then regulated by means of a signal from the optimizer and a control device. The illustrative embodiment is shown for an industrial-scale facility that was charged with 100 m³/h of feedstock and contained 100 m³ of a noble metal reforming catalyst. The products are transferred to a separator operating at low temperatures.

However, conducting investigations in (such) pilot facilities requires considerably greater technical expense than the method according to the invention, which is carried out by means of online characterization and without condensation. This accuracy is of decisive importance with respect to utilization of the data and the method in order to obtain the most accurate possible results concerning the catalytic properties of catalysts and the method. In this context, it is particularly important to take into account that naphtha reforming is a method that is particularly technically demanding, as it relates to the conversion of multicomponent mixtures and a plurality of components is contained in the product fluid. Optimization of the industrial-scale processes is extremely costly, as it is often possible to achieve only minor improvements. These minor improvements, however, are extremely beneficial.

Another advantage of the method according to the invention is that the analytical characterization of the product fluid stream can be carried out directly in each case based on the gaseous samples. It is therefore not necessary for the liquid product components to condense out before the analysis is carried out. This makes it possible to substantially simplify known methods for testing of naphtha reforming. Because of the structural units of the equipment made possible chiefly by dispensing with compressors and condensers, constructing the apparatus according to the invention requires little technical expense. The method according to the invention is therefore preferably characterized in that an online analytical characterization of the product is carried out in a fluid manner, with no previous condensing of the product fluid taking place, in at least one of the reactors arranged in parallel.

Because of the simplified equipment used in the method according to the invention, the method is also particularly well-suited for use in high-throughput facilities equipped with a plurality of reactors arranged in parallel. This has a synergistic effect with respect to the combination of the technical configuration of the method according to the invention in connection with high-throughput test facilities equipped with two or more reactors arranged in parallel.

In particular, it is also preferred to use the method according to the invention in high-throughput facilities equipped with 4 to 40 reactors arranged in parallel. Furthermore, it is preferred to use the method according to the invention in connection with high-throughput facilities equipped with 4 to 20 reactors arranged in parallel.

Such high-throughput facilities with reactors arranged in parallel are characterized in that they can be operated in the research laboratory, wherein the individual reactors arranged in parallel are characterized by a specified catalyst capacity. The catalyst capacity of the reactors is preferably in the range of 0.5-200 cm³, more preferably in the range of 1-100 cm³, and even more preferably in the range of 2-50 cm³.

The method according to the invention is characterized by high long-term stability, and can therefore for example be operated over a period of 10 to 100 days, preferably for a period of 1 day to 180 days, and more preferably for a period of 10 to 90 days. The particular suitability of the method according to the invention for long-term investigations is significant, as this makes it possible to test the catalysts and the reforming method under conditions similar to those of the industrial-scale process.

The use of relatively costly and large-dimensioned pilot facilities for the investigation of naphtha reforming is known in the prior art. The pilot facilities are operated as single-strand plants with larger amounts of catalysts, resulting in extremely high operating costs. The liquid reaction products are condensed in these pilot facilities in order to then determine their anti-knock characteristics (octane number) by means of engine test stands.

The potential of the present method lies in that parallel catalysts in the area of naphtha reforming can be tested with a constant octane number and thus under near-industrial conditions. This can provide clear added value in the development of new catalyst systems, but also in performance comparison of existing catalysts.

It is important in the method according to the invention that online analytical characterization be carried out, with this online analytical characterization being carried out on a gaseous product fluid stream. In particular, it is also preferred that the online analytical characterization of the gaseous product fluid stream be carried out by means of gas chromatography.

Naphtha composition of reactant stream and product stream

The present method relates to the conversion and analysis of multicomponent mixtures, wherein the mixtures contain different hydrocarbon-containing components.

The term naphtha-containing reactant fluid stream or naphtha-containing initial feed means, preferably and within the meaning of the present invention, that said stream has at least one hydrocarbon-containing component from the group with 5 to 14 carbon atoms, and preferably a mixture of hydrocarbon-containing components with 5 to 14 carbon atoms. Moreover, the naphtha-containing reactant fluid stream also comprises hydrogen, with the hydrogen content of the naphtha-containing reactant fluid stream preferably being in the range of 0.5-60 vol. %, and more preferably 10-25 vol. %. The conversion of the naphtha-containing reactant fluid stream produces a reformed gasoline that constitutes a naphtha-containing product fluid stream. The naphtha-containing product fluid stream can comprise a plurality of different hydrocarbon-containing components. For example, the naphtha-containing product fluid stream comprises 1 to 500 hydrocarbon components, preferably 20 to 400 hydrocarbon components, and more preferably 20 to 300 hydrocarbon components.

In a preferred embodiment, the online analytical characterization is characterized by extremely high accuracy with respect to the qualitative and quantitative characterization of a plurality of components. It should also be noted in this connection that a plurality of different product components is generated in the reforming of naphtha in particular.

The essential process parameters of the method according to the invention include the temperature of the individual reactors, the reactor pressure, and the space velocity "WHSV." It is of importance here that each of the individual reactors be equipped with a regulable heating device. The individual heating devices should preferably be regulable independently of one another.

The conversion of the naphtha-containing reactant fluid stream can be carried out at a pressure in the range of 1.2-100 bar, and preferably at a pressure in the range of 1.5-100 bar, and the method according to the invention is more preferably carried out at a pressure in the range of 2-35 bar. The outlet lines of the individual reactors may be connected to a repressurization gas and pressurization gas device.

In a preferred embodiment of the method according to the invention, the method relates to the control of a catalyst testing apparatus for the testing of catalysts in reforming of naphtha that is operated so that the process parameters in connection with the individual reactors are adapted so that one product fluid stream with a constant octane number (specifically the C5+ fraction, i.e. the fraction of hydrocarbons with 5 or more carbon atoms) is discharged in each of the product fluid streams from the individual reactors arranged in parallel.

As analysis units, all technical units can be used that output data that can be correlated with an octane number. As a reference, iso-octane has an octane number of 100, while heptane has an octane number of 0. The octane number serves to characterize the "knocking behavior" of the substance mixture.

It should be noted that the knocking behavior and the octane number connected therewith for individual components and groups are known in the literature, and these known data are included in the method according to the invention. An octane number can be determined by means of analytical characterization, calculation derived therefrom, and comparison with stored data. The octane number is preferably obtained by weighted summation of the amounts of individual components or component groups and their knocking characteristics.

BRIEF DESCRIPTION OF THE FIGURES

FIG. 4 shows a diagram of a controller that is coupled to a system. "System" here refers to a parallel reactor apparatus. The controller receives time-dependent values from the product fluid streams of the individual lines and adapts a process parameter based thereon.

Figure 4:
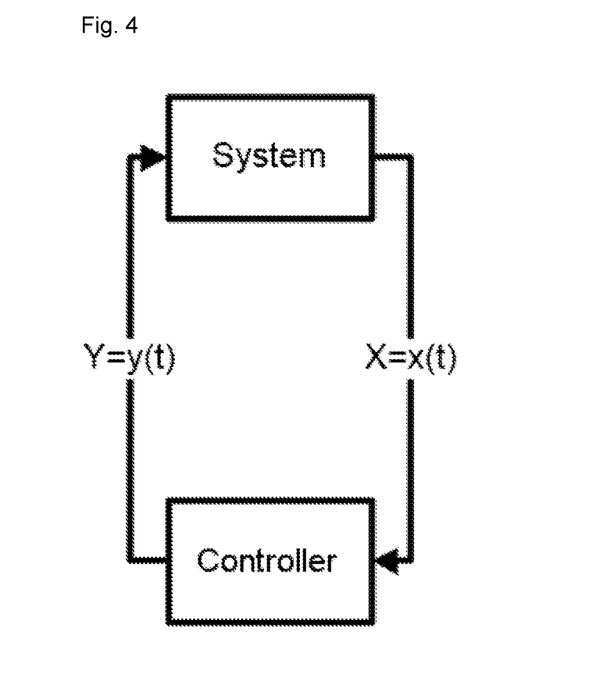
Figure 5:
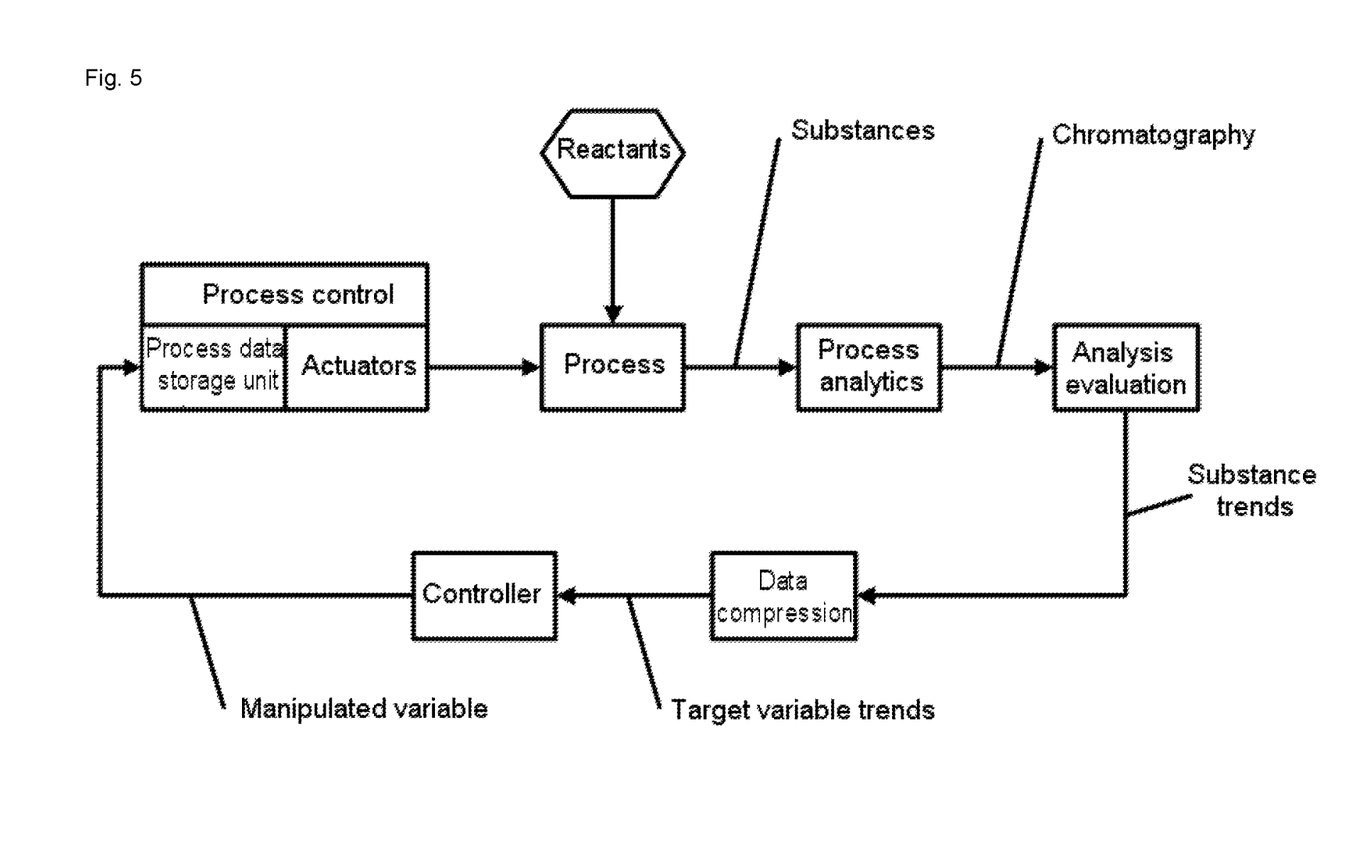
FIG. 5 shows an overview of a control circuit that is a component of a catalyst test device. According to the method of the invention, the control circuit is a component of an apparatus with reactors arranged in parallel.
Figure 6:
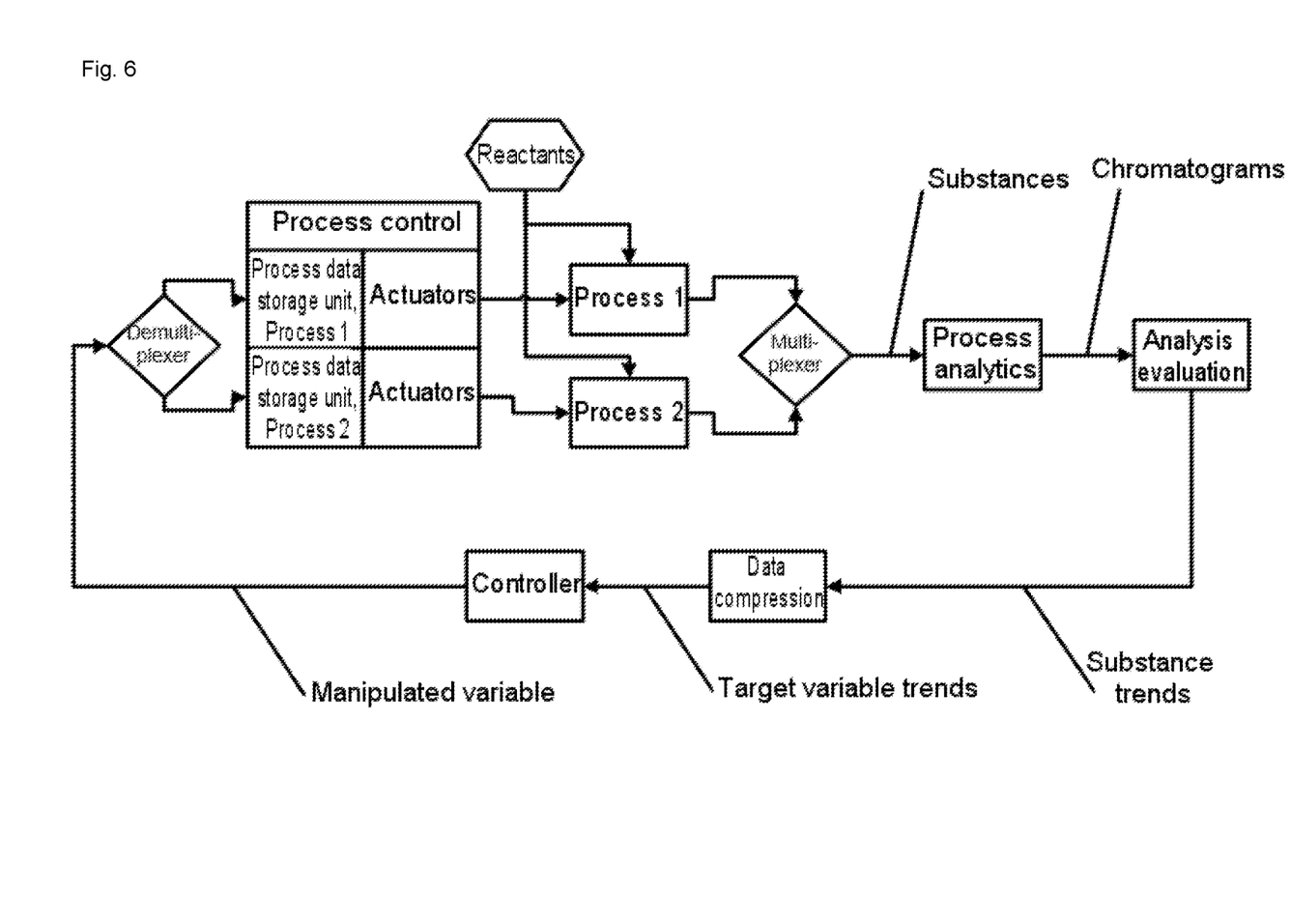
FIG. 6 shows an overview of a control circuit in a process sequence, wherein subdivision is carried out here between process 1 and process 2, which refer to two different reactor units of a catalyst test device respectively.

In all of the embodiments shown in FIGS. 4 through 6, the coupling of the process control relates to the connection with a parallel reactor apparatus.

The term "system" as used herein has no limiting effect, and refers to any arrangement of parallel reactors. The term "process" in FIG. 5 also refers to the method in combination with reactors arranged in parallel.

The number of reactors arranged in parallel is limited by technical manageability with respect to the upper limits on the number of reactors. An aspect of the method according to the invention is the use of two or more parallel reactors, and preferably four or more reactors. The degree of parallelization affects the configuration of the method, as the analysis time in analysis of product fluids is subject to specified minimum times. In addition to the analysis time, other parameters also affect the duration. In particular, the analysis column should preferably be regenerated after analysis is carried out.

There are therefore processing times (durations) for the groups of process analytics, analysis evaluation, and data processing. The duration in these groups is preferably a maximum of half the reaction time of the system (Nyquist-Shannon sampling theorem).

The term "multiplexer" used herein refers to a selection valve by means of which the product fluid streams of the respective reactors are switched on the analysis device sequentially in time (also referred to herein as being "multiplexed"). "Demultiplexing" of the controller means that the manipulated variable determined from the data is assigned to the reactor—and the process taking place in the reactor—that originally provided these data. It can be seen from this that the multiplexers and demultiplexers must occupy the same number of positions.

Figure 1:
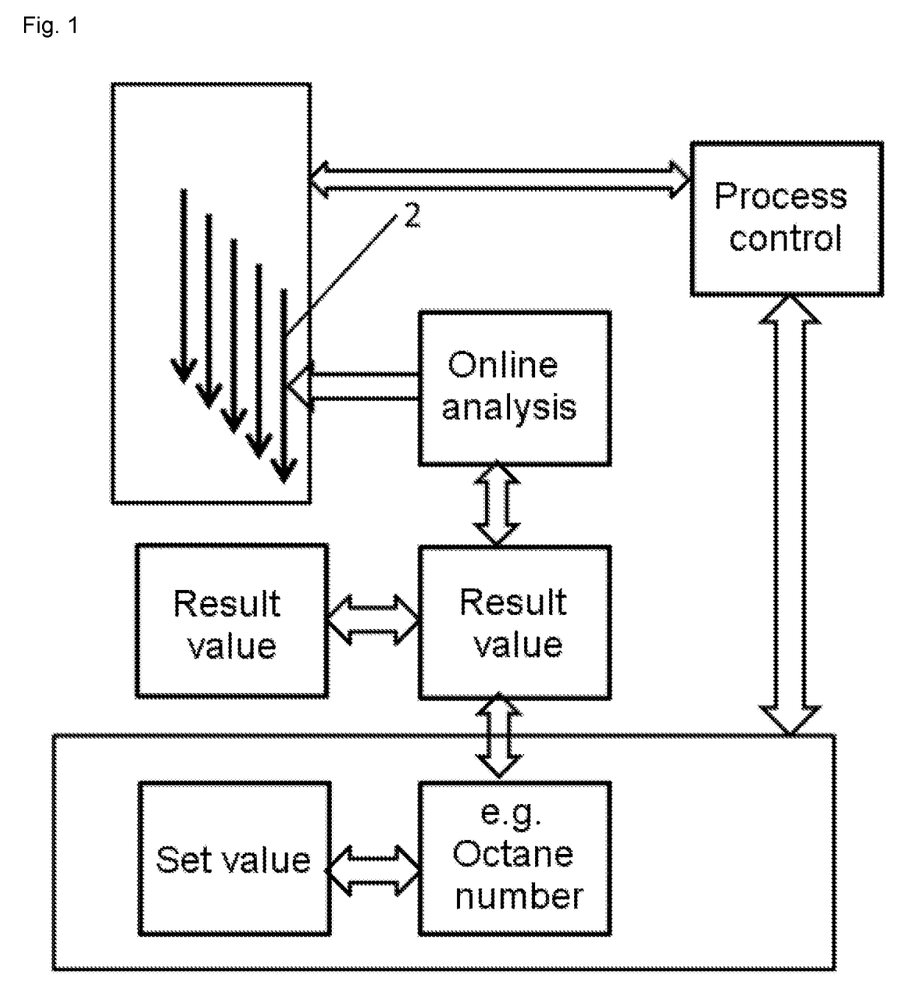
FIG. 1 shows an example of a diagram of the method according to the invention and of the control loop, wherein an online analytical characterization of the product fluid stream from an outlet is first carried out, and at least one result value, and preferably a plurality thereof, is compared to at least one set value, and preferably a plurality thereof. A data analysis is carried out by means of an evaluation model, with adaptation of process parameters being conducted. The control loop is repeated. The octane number in the product fluid stream is preferably kept constant for the duration of the catalytic test investigation by adapting the temperature of the individual reactors.
Figure 2:
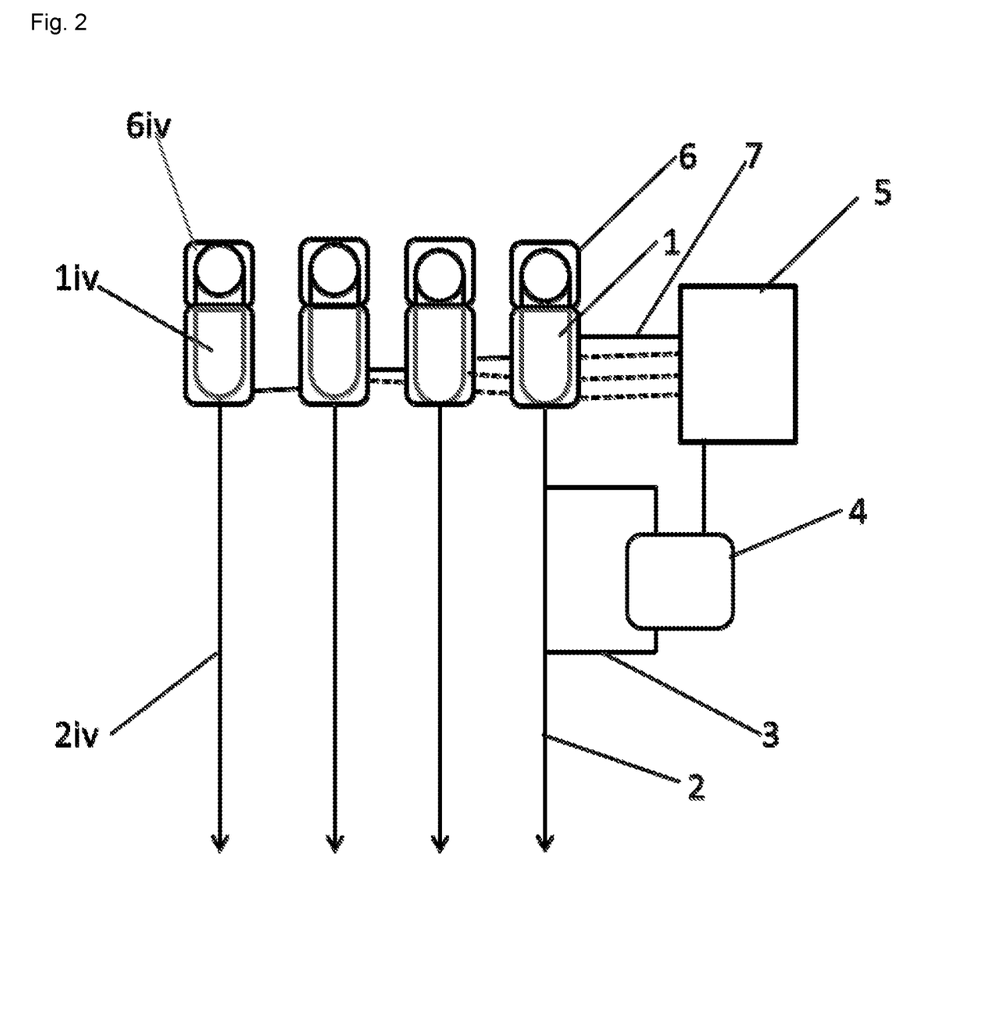
FIG. 2 shows a schematic diagram of an apparatus with four reactors arranged in parallel, which are equipped with an online analysis unit, in which the analysis unit is operatively connected to a partial stream line of the outlet line 1.

In the following, individual process steps of the method according to the invention, as shown in FIGS. 1, 5 and 6, are explained in further detail:

1. A multicomponent mixture of an outlet line of a reactor is separated by means of an online analysis unit into its individual components.
2. The separated individual components show more or less pronounced differences with respect to the retention times, which are connected with time trends.
a. The analytical evaluation is preferably connected with a grouping of analysis data according to boiling ranges, and the result of this evaluation is preferably used for determination of the octane number. Data compression to an individual value is particularly preferred in this case. It is necessary for the actual controller to be supplied only with a time-dependent input variable. Moreover, the data compression preferably takes place in a model-based manner. In connection with the method according to the invention, the model consists of compression of the analytical characterization data, preferably determined by means of online gas chromatography, to an octane number. Moreover, it is also conceivable for the analytical characterization to take place by means of IR spectroscopy.
3. The controller is an element of the apparatus that reacts to a parameter in a time-dependent manner.
a. In the specific case, the controller in particular:
i. is programatically represented (is an algorithm)
ii. is configured as an interval-controlled search and approximation algorithm.
iii. Alternatives: Simplex search algorithm, other search algorithms are also included in the present invention.

By means of the process analytics, in the case of chromatographic methods, images of the processes are produced in a time-discrete manner. At specified intervals, i.e. the sampling frequency, individual samples are taken of the substance mixtures (i.e. of the reformates) coming from the respective reactor.

The substance mixtures are analyzed, i.e. decomposed into their components. In naphtha reforming and the method according to the invention, it is particularly preferred to carry out a gas chromatographic analysis at this point. The gas chromatographic analysis can be considered to be incomplete chromatography, as the substance mixture is broken down into groups whose mutual demarcation is carried out by means of a characteristic known substance.

A part of the method according to the invention is therefore that a plurality of time trends is compressed to a single time trend. The actual value of the octane number is preferably entered into the controller (specifically as function x=octane number(t)). Instead of the term octane number, one can also use the term research octane number, abbreviated as RON.

A controller within the meaning of the present invention can process exactly one input variable. For this reason, if the system to be controlled yields a plurality of actual values, these must be condensed to a single time-dependent variable.

A controller can control exactly one system. In this case, the response of the controller (manipulated variable) can be distributed among a plurality of actuators and thus a plurality of influencing possibilities. For example, the temperature and the flow of a reactor can be switched to the same controller output and thus the same manipulated variable. The system then responds to all influencing variables simultaneously.

Two or more controllers are preferably used to influence the temperature of a reactor. In this case there should preferably be the same number of systems as controllers (thermosensor (1); controller (2); actuator (3); heating element (4); thermosensor (1)). In order for the control(s) to function, one must ensure that the mutual influence of the controllers on one another is sufficiently small. If a particular threshold for mutual influence is exceeded, the systems may begin to vibrate. As a rule, these vibrations are undesirable, as critical operating states may be reached.

Examples

Figure 3:
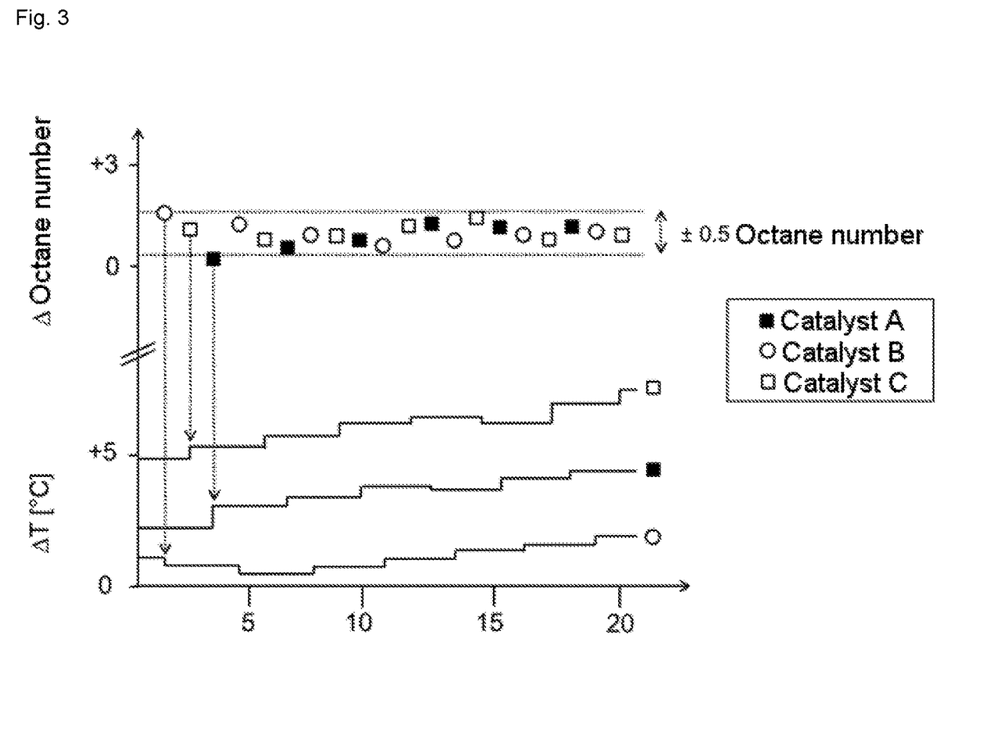
FIG. 3 shows in the upper part of the y axis a schematic diagram of the octane number values (which are kept constant while the temperatures of the different catalysts are built into three reactors arranged in parallel), with the measurements being tracked over a period of 10 hours. The tracking of the temperature of the respective reactor heater for the respective catalysts is given in the lower part of the y axis. The x axis represents this time period required in order to keep the octane number of the C5+ hydrocarbons at a constant level.

In order to illustrate the method according to the invention, a test run was carried out with five different catalysts under the conditions of naphtha reforming. Industrially manufactured catalysts were used, specifically approx. 9 g of catalyst for each reactor. The duration of the investigation was 200 hours, with the results shown in FIG. 3 being a section of a time range of 10 hours. The individual experiments were carried out such that the octane number was kept constant, which can be seen in the upper part of FIG. 3. The temperature of the individual reactors was constantly increased in order to compensate for the loss of activity seen in connection with catalyst ageing. On average, the temperature over the time interval of 200 hours was increased each time by 1.5 to 5° C. in order to keep the octane number of the product fluid stream in a constant range. The measurement values for the octane number show a standard deviation of ±0.3. It should be noted that this is an extremely small standard deviation that has not been published in the literature in this manner with laboratory equipment. The high accuracy is of great significance with respect to the technical reliability of the data achieved by means of the method according to the invention.

LIST OF REFERENCE NUMBERS

1—Reactor 1
1*iv*—Reactor 4
2—Outlet line connected to reactor 1
2*iv* Outlet line connected to reactor 4
3 Partial stream line
4—Online analysis unit
5 Process control
6—Reactor heater for reactor 1
6*iv*—Reactor heater for reactor 4
7—Connection of process control to reactor heater 1

The invention claimed is:

1. An apparatus for investigating naphtha reforming, the apparatus comprising:
a plurality of reactors each having a reaction chamber arranged in parallel;
a product fluid supply common to one or a plurality of these reactors;
a process controller; and
an analysis unit,
wherein:
each individual reactor has an outlet line that discharges a product fluid stream;
each individual reactor is equipped with an individually controllable heating device;
each individual reactor has a catalyst capacity in the range of 0.5 to 200 cm$^3$;
the analysis unit is operatively connected to each outlet line, and the analysis unit is electrically connected to the process controller; and
the analysis unit analyzes a gaseous product fluid stream, and the analysis unit, together with the process controller, allows the determination and optimization of an octane number in the plurality of reactors arranged in parallel.

2. The apparatus as claimed in claim 1, wherein the analysis unit is an online analysis unit.

3. The apparatus as claimed in claim 1, wherein the plurality of reactors are tubular reactors.

4. The apparatus as claimed in claim 1, wherein the apparatus has a number of 2 to 40 reactors arranged in parallel.

5. The apparatus as claimed in claim 1, wherein the individual reactors have a catalyst capacity in the range of 1 to 100 cm$^3$.

6. The apparatus as claimed in claim 1, wherein a temperature sensor is arranged in parallel in the interior of at least one of the reactors.

7. The apparatus as claimed in claim 1, wherein the outlet lines of the individual reactors are equipped with membrane valves and the pressure inside the reactors is controlled by adjusting the membrane valve.

8. A method for investigating naphtha reforming using an apparatus as claimed in claim 1, the method comprising:
(i) supplying a naphtha-containing reactant fluid stream containing at least one hydrocarbon from the group with 5 to 14 carbon atoms, and hydrogen with a hydrogen content in the range of 0.5-60 vol. % to the individual reactors;
(ii) contacting the naphtha-containing reactant fluid stream in the respective reactors with a catalyst at a temperature in the range of 100° C. to 600° C., to convert the naphtha-containing reactant fluid stream to one product fluid stream each;
(iii) supplying this product fluid stream to an outlet line;
(iv) analytically characterizing the individual product fluid streams with the analysis unit, wherein the analysis quantifies one or a plurality of components, to obtain a result value;
(v) comparing the result value with a set value, wherein the comparison comprises the storage of an evaluation model;
(vi) adapting a process parameter that relates to the reaction process of the respective reactor from the outlet line of which the product fluid stream was analyzed; and
repeating the process steps (iv) through (vi) by analyzing the product fluid stream that is discharged from the respective outlet lines.

9. The method for investigating naphtha reforming as claimed in claim 8, wherein the product fluid stream contains less than 1% of condensed product fluid.

10. The method for investigating naphtha reforming as claimed in claim 8, wherein the process parameters are pressure in one of the reactors, temperature of a reactor heater, and/or flow rate of the reactant fluid stream of a feed supply.

11. The method for investigating naphtha reforming as claimed in claim 8, wherein the duration of the analytical characterization is in a range of 0.1 min to 300 min.

12. The method for investigating naphtha reforming as claimed in claim 8, wherein the method is carried out over a duration of 24 h to 3000 h.

13. The method for investigating naphtha reforming as claimed in claim 8, wherein the evaluation model relates to calculation of the octane number and the method is such that adaptation of the process parameters is carried out so that the octane number of the reformate in the product fluid stream has a predetermined target value, wherein the target value of the octane number is kept constant for the duration of the method.

14. The method for investigating naphtha reforming as claimed in claim 8, wherein the contacting (ii) is carried out at a pressure in the range of 1.2 to 100 bar.

15. The method for investigating naphtha reforming as claimed in claim 8, wherein the naphtha reforming is carried out for optimization of the process conditions.

* * * * *